US005332399A

United States Patent [19]

Grabenkort et al.

[11] Patent Number: 5,332,399

[45] Date of Patent: Jul. 26, 1994

[54] SAFETY PACKAGING IMPROVEMENTS

[75] Inventors: Richard W. Grabenkort, Barrington; Ralph M. Quinn, Ingleside, both of Ill.

[73] Assignee: Abbott Laboratories, Abbott Park, Ill.

[21] Appl. No.: 811,588

[22] Filed: Dec. 20, 1991

[51] Int. Cl.[5] .......... A61B 19/00

[52] U.S. Cl. .......... 604/415; 604/403

[58] Field of Search .......... 604/403, 404, 415, 416, 604/83, 85, 86, 202

[56] References Cited

U.S. PATENT DOCUMENTS

| | | | |
|---|---|---|---|
| 4,614,267 | 9/1986 | Larkin . | |
| 4,614,515 | 9/1986 | Tripp et al. | 604/416 X |
| 4,703,864 | 11/1987 | Larkin . | |
| 4,746,017 | 5/1988 | Howard et al. | 604/404 X |
| 4,757,911 | 7/1988 | Larkin . | |
| 4,781,679 | 11/1988 | Larkin . | |
| 4,784,259 | 11/1988 | Grabenkort . | |
| 4,784,658 | 11/1988 | Grabenkort | 604/416 X |
| 4,936,445 | 6/1990 | Grabenkort . | |
| 4,948,000 | 8/1990 | Grabenkort . | |
| 4,982,769 | 1/1991 | Fournier et al. | 604/416 X |
| 4,982,875 | 1/1991 | Pozzi et al. | 604/416 X |
| 5,064,059 | 11/1991 | Ziegler et al. | 604/416 X |

*Primary Examiner*—Robert A. Hafer
*Assistant Examiner*—Sam Rimell
*Attorney, Agent, or Firm*—A. Nicholas Trausch

[57] ABSTRACT

Packaging of highly toxic materials entails incorporating safety improvement so as not to endanger patients and health care workers. Such safety improvements include the use of suitable sealing members between the glass vials and the protective covering therefor and various means to ensure that vials of highly toxic materials can not be inadvertently interconnected to single treatment I.V. bags, for instance, by making the connecting means on the vials and the single treatment diluent bags incompatible with one another.

5 Claims, 5 Drawing Sheets

SAFETY PACKAGING IMPROVEMENTS

BACKGROUND OF THE INVENTION

In the health-care field, particularly as to the storage, intermixing, and administration of medicaments, Abbott Laboratories has been one of the pioneers with its ADD-Vantage® line of products which includes sealed, flexible, clear plastic bags of various diluents and sealed vials of various medicaments interconnectible therewith whenever desired but without intermixing of the contents thereof until desired, both the bags of diluents and the vials of medicaments being readily storable and having a good shelf life. These diluent bags have sleeve-like inlet ports sealed in an upper edge thereof with stopper-gripping closures at the inner ends thereof with most of the sleeve-like ports being provided with internal threads which are complementary to external threads provided on neck portions of the vials to facilitate interconnection thereof. The vials are preferably provided with a plastic two-part cover which fits over the neck and upper portions of the vial to provide sterile protection of the stopper which has a central recess which is adapted for engagement with the stopper-gripping closure of the bag port. The lower edge of the two-part cover interfits with the upper edge of a plastic shroud which fits over the lower portion of the vial and which has an opening and a pull-out hanger in its bottom surface for supporting the vial in an inverted position. An annular frangible section interconnects the lower portion of the cover and the upper portion which is characterized by a reduced-thickness needle access section which is aligned with the central recess of the stopper whereby the medicament in the vial, if same is in liquid form, may also be extracted from the vial by a piercing-needle syringe. When the vial is to be interconnected with a bag of diluent, the upper tear-away portion of the cover is first removed to expose the stopper and the threads on the neck portion of the vial, after which it is rotatably tightened into the sleeve-like port with the recessed stopper fitting over and engaging the stopper-gripping closure of the bag port. The medicament remains isolated from the diluent until such time that the bag port closure is disengaged from the port with the stopper engaged therewith being simultaneously removed from the vial to permit intermixing of the medicament and the diluent. The bag port closure is disengaged by manipulation thereof from outside of the flexible walled bag.

This ADD-Vantage system is disclosed in the following listed U.S. patents, all of which are incorporated herein by reference:

| U.S. Pat. No. | Date |
|---|---|
| 4,614,267 | September 30, 1986 |
| 4,614,515 | September 30, 1986 |
| 4,703,864 | November 3, 1987 |
| 4,757,911 | July 19, 1988 |
| 4,781,679 | November 1, 1988 |
| 4,784,259 | November 15, 1988 |
| 4,784,658 | November 15, 1988 |
| 4,936,445 | June 26, 1990 |
| 4,948,000 | August 14, 1990 |

A new product line of Abbott Laboratories known as the ADD-Vance line, is directed to the storage, intermixing, dispensing and controlled administration of highly toxic materials which are packaged in vials similar to the vials of the ADD-Vantage line. However, in view of the extreme toxicity of these ADD-Vance drugs, which are primarily chemotherapeutics, the danger to both patients and health care workers is of extreme importance. These highly toxic materials require vials that are sealed to a greater degree than the requirements for mere sterility so as to protect health-care workers handling same and it is imperative that such highly toxic material vials not be interconnectible with single treatment diluent bags as same would be life-threatening if this occurred and the resulting mixture was administered to a patient.

SUMMARY OF THE INVENTION

The new and unobvious safety packaging improvements developed for the highly toxic material vials of the present invention, which vials are generally similar to the vials for materials of normal toxicity except that they have a greater length and thus a greater volume, include completely encasing these similar vials in a plastic cover/shroud wherein a portion of each cover is removable to expose the stopper sealing the open end of the vial whereby either minute portions of the highly toxic material, if in liquid form, may be extracted from the vial using a piercing-needle syringe or the highly toxic material vial may be interconnected with a special bulk or multi-treatment diluent bag having a mating sleeve-like port, providing an annular sealing member between the vial and the cover/shroud at a critical point therebetween, and by modifying the thread on the neck of the similar vial in any one of several different ways to ensure that it is not rotatably connectible in the port of a single treatment diluent bag, for instance, by providing only left-hand threads on the vials for highly toxic materials whereas all of the single treatment diluent bags have vial-receiving ports with right-hand threads or by providing the vials for highly toxic materials with threads, either right or left-handed, of a different size or helix than those in the ports of the single treatment diluent bags.

Therefore, the present invention is directed to new and novel safety packaging improvements for vials containing highly toxic materials whereby to minimize the possibility of exposure thereto by both patients and health-care workers.

BRIEF DESCRIPTION. OF THE DRAWINGS

The features which are believed to characterize this invention are set forth in the appended claims. The invention itself, together with its features, objects and attendant advantages, will be best understood by reference to the following detailed description of a presently preferred embodiment thereof, taken in conjunction with the accompanying drawings, in which:

Figure 1:
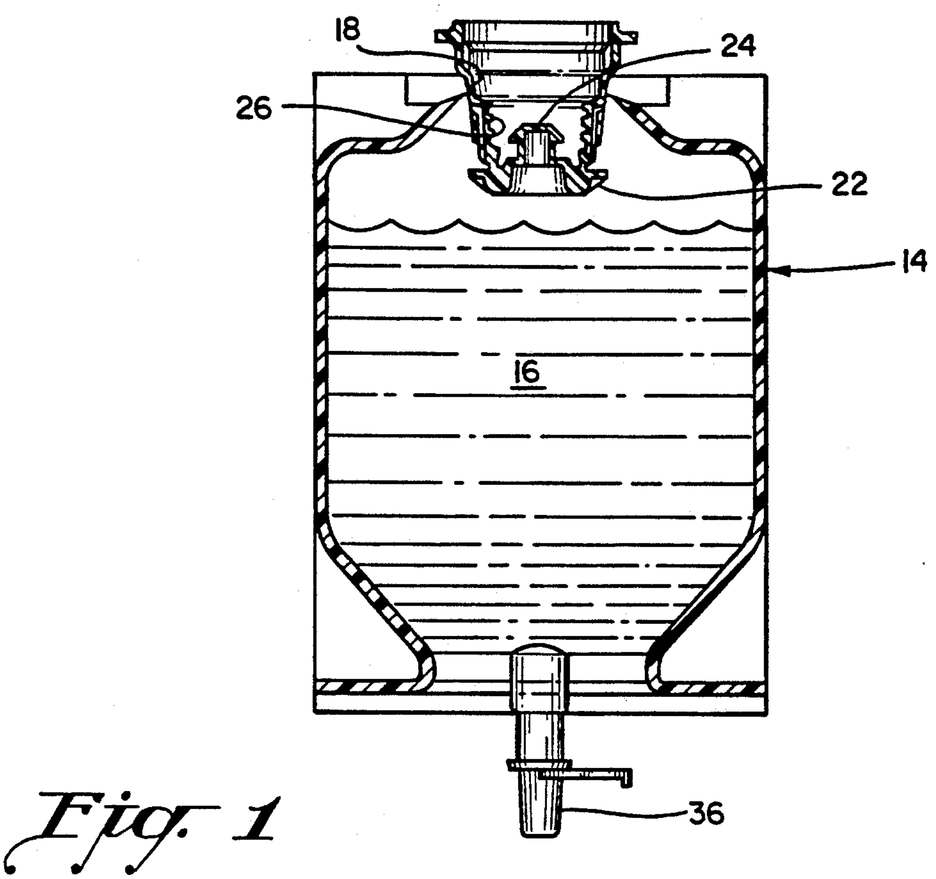
Fig. 1 (PRIOR ART)
FIG. 1 is an elevational view, partially in vertical section, of a single treatment diluent bag known in the prior art.
Figure 4:
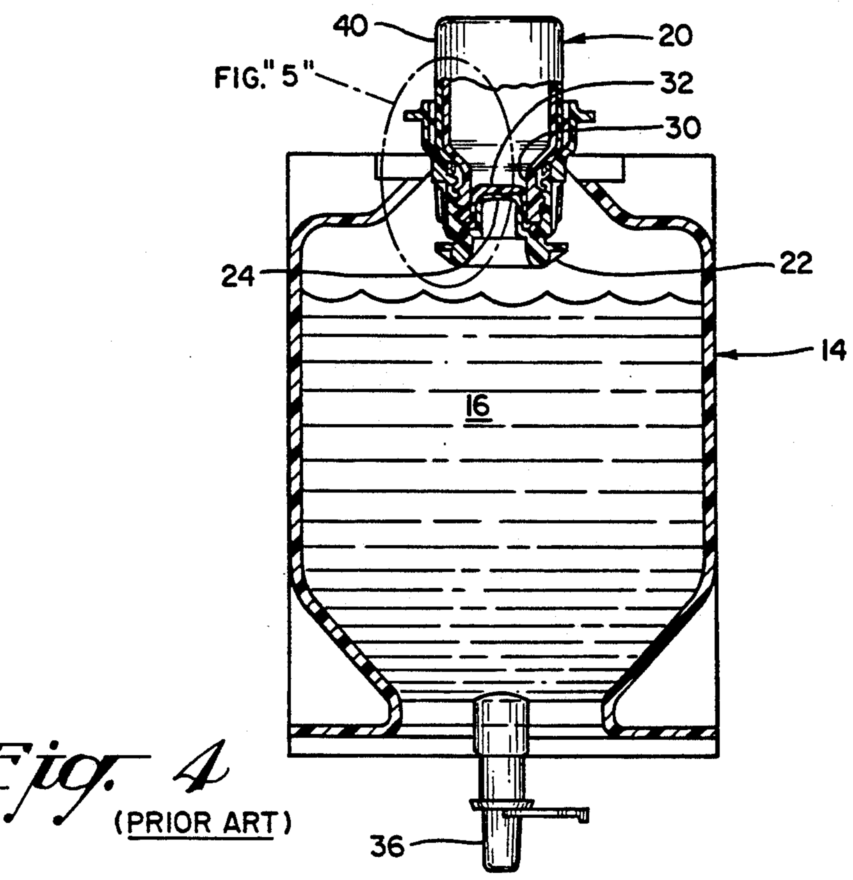
Fig. 4 (PRIOR ART)
FIG. 4 is an elevational view, partially in vertical section, showing the prior art vial, as shown in FIG. 3, interconnected with the prior art diluent bag of FIG. 1.
Figure 6:
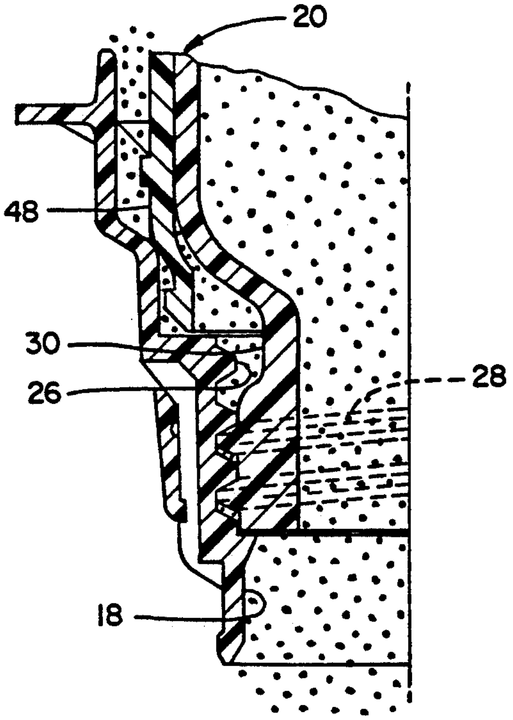
Fig. 6 (PRIOR ART)
FIG. 6 is a view similar to FIG. 5 after removal of the stopper-gripping closure from the inner end of the diluent bag port and the simultaneous removal of the gripped-stopper from the vial, all as is known in the prior art.
Figure 7:
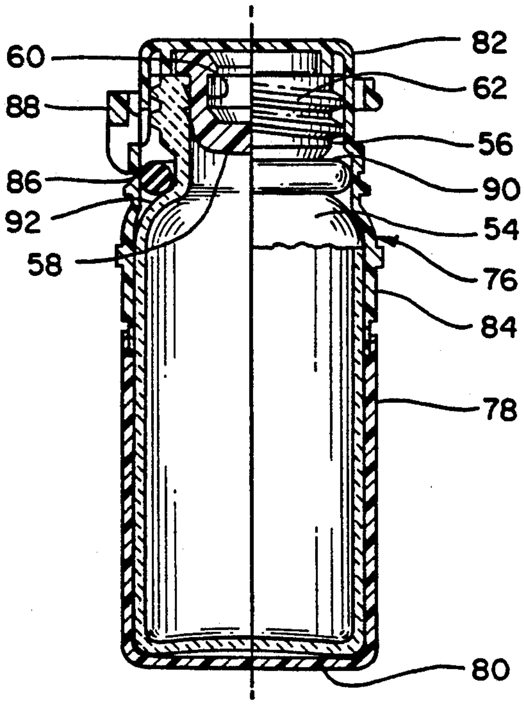
FIG. 7 is an elevational view, partially in vertical section, of a vial for highly toxic materials provided with the safety packaging improvements embodying a preferred form of the invention, the vial of FIG. 7 being comparable to the vial of FIG. 2 for medicaments of normal toxicity.
Figure 8:
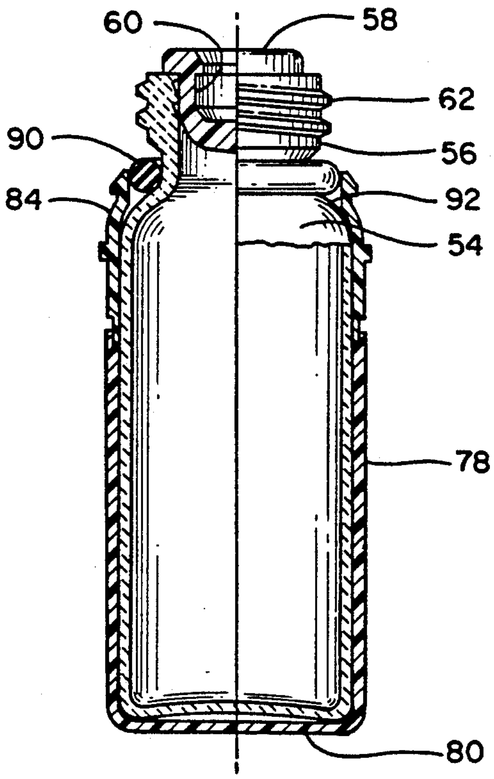
FIG. 8 is a view similar to FIG. 7 with the upper part of a two-part cover broken away to expose the stopper and the left-hand threaded neck portion, FIG. 8 being comparable to FIG. 3.
Figure 9:
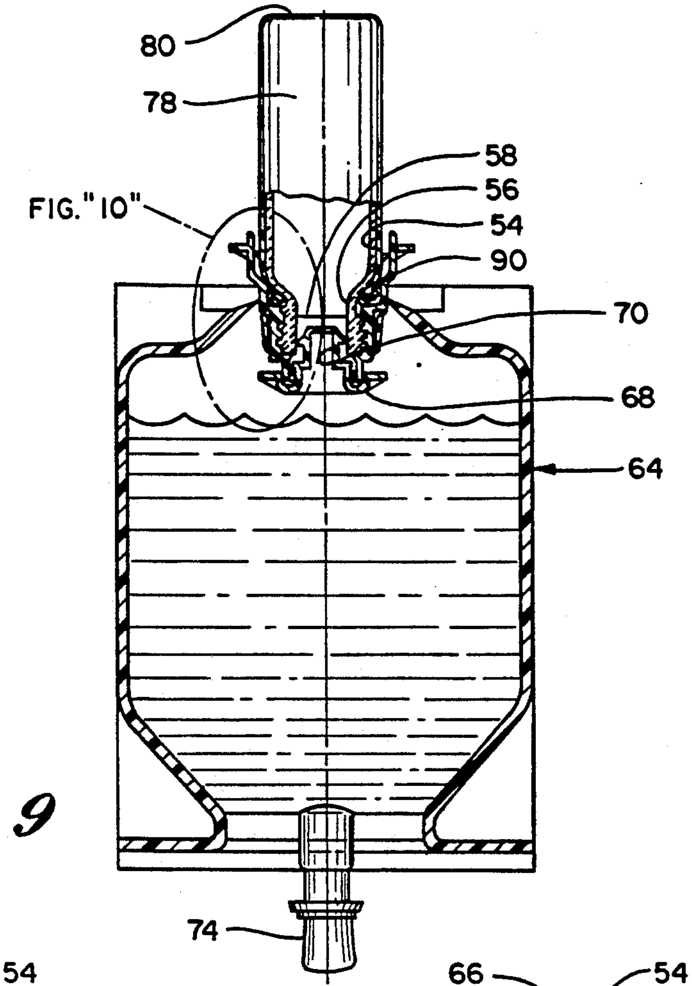
FIG. 9 is a view similar to FIG. 4 with the vial for highly toxic materials, as shown in FIG. 8, interconnected with a multi-treatment diluent bag especially adapted for dispensing highly toxic materials.
Figure 10:
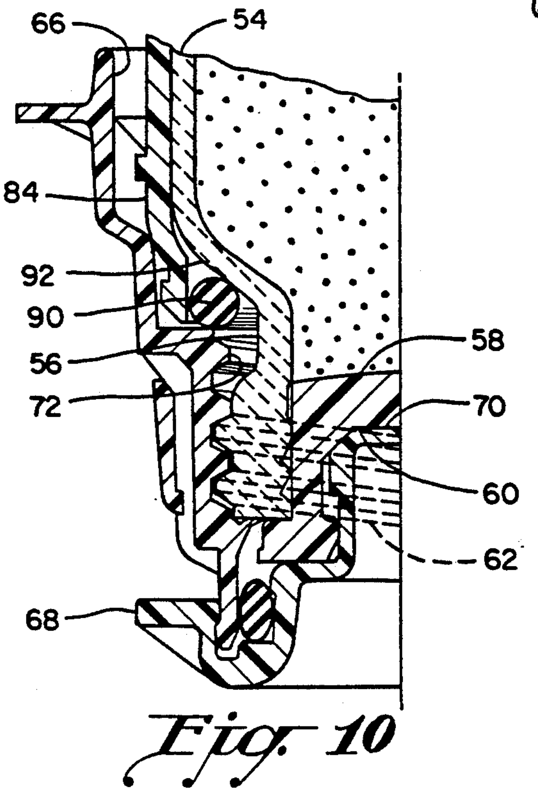
FIG. 10 is an enlarged vertical section of the portion of FIG. 9 encircled by a broken line with the stopper sealed in the highly toxic material vial, FIG. 10 being comparable to FIG. 5.
Figure 11:
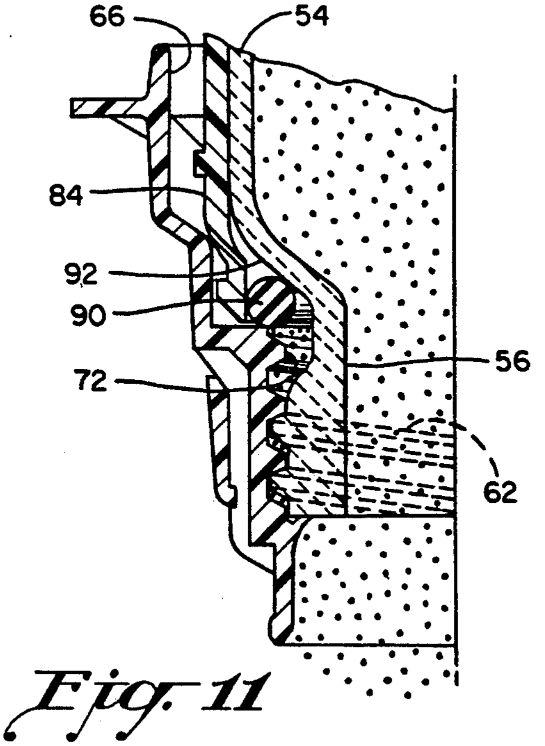
Figure 12:
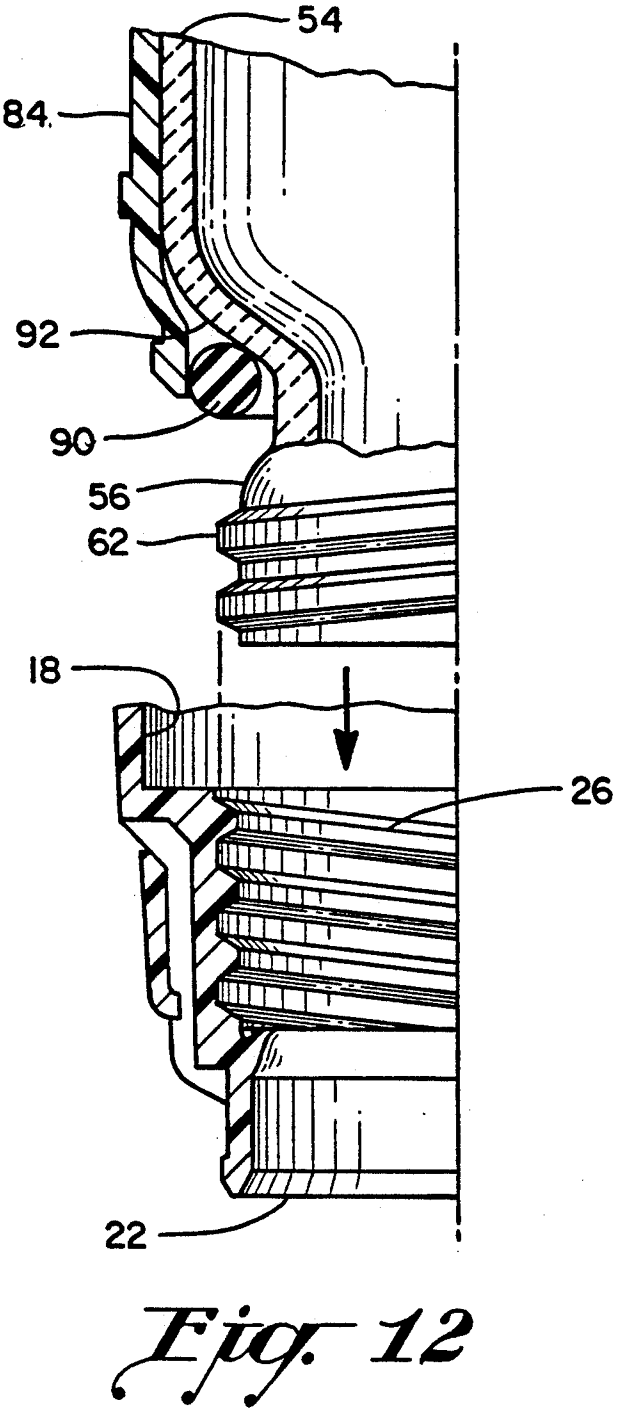

FIG. 11 is a view similar to FIG. 10 and comparable to FIG. 6 after simultaneous removal of the bag port closure and the vial stopper; and FIG. 12 is a view, partially in elevation and partially in vertical section, illustrating why the highly toxic material vial with a left-handed thread of FIGS. 7, 8, and 9 is not interconnectible with the port of the single-treatment diluent bag of FIGS. 1 and 4 which has a right-handed thread.

DESCRIPTION OF THE PREFERRED EMBODIMENT

Figure 2:
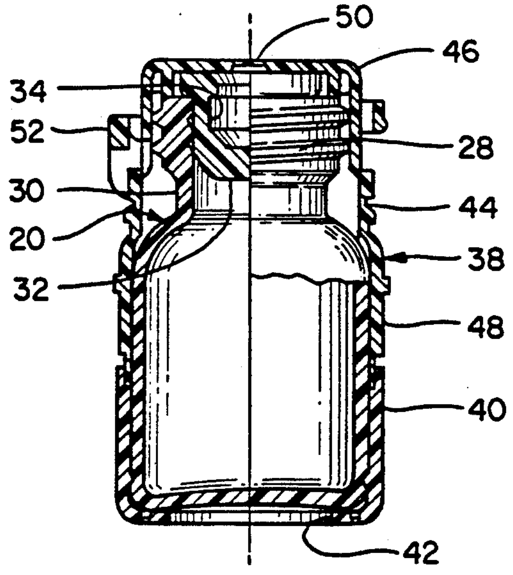
Fig. 2 (PRIOR ART)
FIG. 2 is an elevational view, partially in vertical section, of a vial for medicaments of normal toxicity for use with the diluent bag FIG. 1, which vial is provided with a protective two-part cover and shroud and is also known in the prior art.
Figure 3:
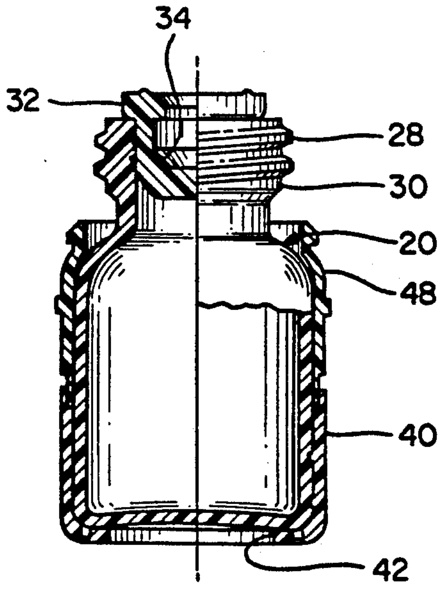
Fig. 3 (PRIOR ART)
FIG. 3 is a view similar to FIG. 2 with the upper part of the protective cover broken away to expose the vial stopper and the threaded neck portion so as to permit interconnection of the vial with the diluent bag of FIG. 1.

With reference to the drawings, FIGS. 1-6 illustrate a system known in the prior art wherein a sealed, flexible, clear plastic bag 14 of diluent 16 having a sleeve-like inlet port 18 sealed in its upper edge is adapted to receive in the port 18 the stoppered end of a vial 20 of medicament of suitable strength for intermixing thereof when desired. The inner end of the bag port 18 is normally closed by a removable closure 22 which is provided with a stopper-gripping member or barb 24 which projects upwardly into the port 18. The port 18 is also internally threaded with a thread 26 which is complementary to a mating thread 28 provided on a neck portion 30 of the vial 20 whereby the medicament vial 20 may be rotatably interconnected with the inlet port 18 of the diluent bag 14. The vial 20, which may be formed of glass, is normally sealed by a stopper 32 having a centrally disposed recess or socket 34 which is automatically engageable with the barb 24 on the port closure 22 when the vial 20 is tightened into the port 18. Thus, when the closure 22 is removed from the inner end of the port 18 the vial stopper 32 is simultaneously removed from the vial 20 permitting the contents of the vial 20 to intermix with the diluent 16 for administration to a patient through a suitable tube set (not shown) connected to an exit port 36 provided at the bottom of the bag 14. As best shown in FIGS. 2 and 3, the glass vial 20 is partially enclosed by a two-part cover 38 which fits over the upper end of the vial 20 in order to provide sterility of the stoppered end of the vial 20 with the lower edge of the two-part cover 39 interfitting with the upper edge of a shroud 40 which fits over the lower end of the vial 20. The bottom of the shroud 40 is open and provided with a pop-up hanger 42 which may be used to support the vial 20 in an inverted position from a suitable support (not shown) at a patient's bedside, the diluent bag 14 being suspended from the vial 20 through the interconnection between the vial neck portion 30 and the bag port 18. The two-part vial cover 38 is characterized by an annular frangible portion 44 which is disposed between an upper cover portion 46 and a lower cover portion 48 and below the neck portion threads 28. The top wall of the upper cover portion 46 is provided with a reduced-thickness wall portion 50 which is aligned axially of the vial 20. Thus, in addition to its interaction with the diluent bag 14, medicament in liquid form may be withdrawn from the vial 20 by using a known-type of stopper-piercing needle syringe (not shown). For additional security, the upper cover portion 46 is retained on the vial neck portion 30 by a ring-clamp 52. Thus, before interconnecting the vial 20 in the port 18 of the bag 14, the ring-clamp 52 is released and the tear-away upper cover portion 46 is removed, thus exposing the stopper 32 and the vial threads 28.

This very popular system for storing, transporting, intermixing and administering medicaments of normal toxicity was developed and pioneered by Abbott Laboratories of North Chicago, Illinois whereby various medicaments and diluents could be packaged, stored, and transported separately and only intermixed just prior to the administration thereof to a patient, the shelf life of the separately packaged materials being much greater than after intermixing thereof. This Abbott product line is known and marketed as the ADD-Vantage line. The medicament vials 20 may be interconnected with the diluent bags 14 well before use, if more convenient, with no intermixing of the contents thereof. Intermixing occurs only after simultaneous removal of the port closure 22 from the inner end of the port 18 and the stopper 32 from the vial 20, the closure 22 being removed by manual manipulation thereof from outside of the bag 14 through the flexible walls thereof.

The storage, intermixing, dispensing and controlled administration of highly toxic materials requires vials that are sealed to a greater degree than the vials 20 containing material of normal toxicity so as to protect health-care workers handling same. As some highly toxic materials may be packaged in glass vials 54, FIGS. 7, 8 and 9, which are similar in appearance to the previously described vials 20, it is imperative that such highly toxic materials vials 54 not be interconnectible with single treatment I.V. bags, such as the diluent bags 14 described herein, as the consequences of such a mix-up could be life-threatening if the resulting mixture were administered to a patient. This non-interconnectibility requirement is absolutely necessary as the similarity of the vials 20 and 54 could result in such a disaster as a result of a mistake made by inexperienced health-care workers or even by experienced health-care workers during an emergency situation or while over-tired or under stress.

Therefore, new, novel and unobvious safety packaging improvements have been provided for Abbott Laboratories' new line of packaged vials 54 for the storage, intermixing, dispensing and controlled administration of highly toxic materials, which line is known as the ADD-Vance line.

As best illustrated in FIGS. 7, 8 and 9, the major visual difference between the highly toxic material vials 54 and the vials 20 for materials of normal toxicity is that the former have a greater axial length and thus can contain a greater volume of materials. As with the vials 20, the vials 54 have open neck portions 56 tightly sealed by a stopper 58 having a barb-engageable recess or socket 60, which stopper 58 may be coated with TFE. The neck portion 56 is provided with an external thread 62 which is specifically designed to be non-mating or incompatible with the internal port thread 26 of the single treatment diluent bag 14. The size or helix of the thread 62 could also be different than that of the port thread 26 or the direction of the thread spiral of the thread 62 could be opposite that of the port thread 26. For instance, if the port thread 26 were a right-hand thread, the vial thread 62 would be a left-hand thread, or vice versa. Such an incompatible situation is illustrated in FIG. 12.

However, as illustrated in FIG. 9, a bulk material or multi-treatment diluent bag 64 for highly toxic materials may be provided which has a sleeve-like inlet port 66 including a closure 68 having a stopper-engaging barb 70 for the stopper socket 60 and an internal thread 72 which is complementary to the thread 62 on the neck portion 56 of the highly toxic material vial 54 to permit interconnection therebetween. A dispensing valve 74 is provided at the bottom of the highly toxic material storage bag 64 to permit dispensing measured quantities of such material therefrom.

Referring again to FIGS. 7 and 8, the highly toxic materials vials 54 are fully encapsulated by a two-part cover 76 and shroud 78 enclosure wherein the bottom wall 80 of the shroud 78 is solid for two reasons. First, it results in a more effective sealing of the encapsulated vial 54, particularly as to the stoppered end thereof wherein the highest degree of sterility is required due to the high toxicity of the materials in the vial 54 and, second, to eliminate the pop-up hanger of the vial 20 as any vial of highly toxic material should not be hangable at a patient's bedside as part of an I.V. arrangement. The two-part cover 76 includes an upper portion 82 which overlies the stoppered end of the vial 54 and a lower portion 84 which interfits with the shroud 78, the two portions 82 and 84 being interconnected by an annular frangible section 86. It is noted that the upper cover portion 82 overlying the stopper 58 is not provided with a reduced-thickness needle access section, as at 50 in the upper cover portion 46 (FIG. 2) for the normal toxicity vial 20, as such highly toxic materials should not be withdrawn from the vial 54 by means of a stopper-piercing needle syringe and health-care workers should be discouraged by every means possible from doing so. A ring-clamp 88 is provided as a further aid in retaining the upper cover portion 82 on the vial 54.

A further safety packaging improvement for the highly toxic material vial 54 is an annular 0-ring sealing member 90 which is seated between the neck portion 56 of the vial 54 adjacent a shoulder 92 thereof and the inner surface of the two-part cover 76 adjacent the frangible section 86 thereof. With the fully encapsulated vial 54, as shown in FIG. 7, the sealing member 90 further ensures sterility of the stoppered end of the vial 54 from any impurities that might have been trapped between the outer surface of the vial 54 and the cover/shroud 76, 78 during fitting of the cover 76 over the upper portion of the vial 54.

Figure 5:
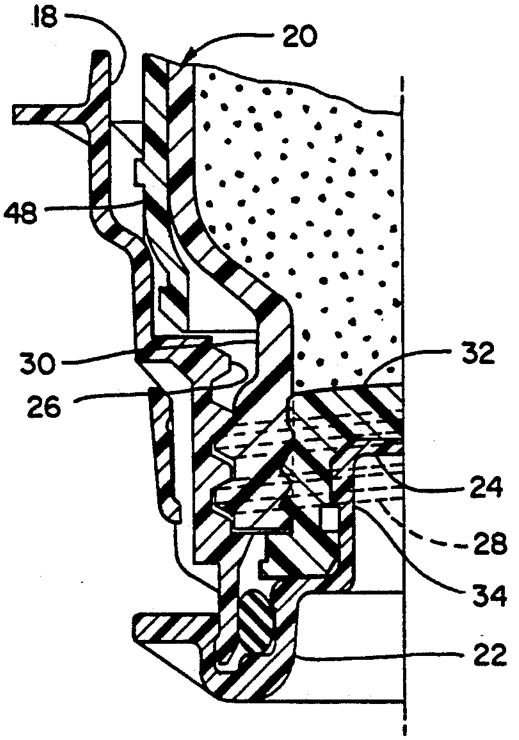
Fig. 5 (PRIOR ART)
FIG. 5 is an enlarged vertical section of the portion of FIG. 4 encircled by a broken line with the stopper sealed in the vial.

The sealing member 90 provides a further sealing function when the highly toxic material vial 54 is interconnected with the sleeve-like inlet port 66 of the bulk or multi-treatment bag 64, as in FIG. 9. Referring first to FIGS. 5 and 6 of the normal toxicity system of the prior art, it is noted that when the port closure 22 and the vial stopper 32 are simultaneously removed (FIG. 6), although the major portion of the normal toxicity contents of the vial 20 enters the diluent bag 14, some of such material may escape by passing through the port and vial threaded portions 28, 30 and then past the edge of the lower cover portion 48 and between the inner surface of the port 18 and the outer surface of the lower cover portion 48 whereby a health care worker could be exposed thereto. If this escaped material were highly toxic, the results could well be life-threatening. This leakage would be especially bad if the vial 20 were not properly tightened in the port 18.

Referring now to FIGS. 10 and 11 wherein the highly toxic material vial 54 has the sealing member 90 provided therein, it is clearly shown that after simultaneous removal of the port closure 68 and the vial stopper 58, although there might be some leakage of the highly toxic material through the vial and port threads 62, 72 further escape and possible life-threatening contact with a health care worker is prevented by the sealing member 90.

Should none of the foregoing safety packaging improvements be in place, another safety packaging improvement that would be effective in preventing intermixing of a highly toxic material from a vial 54 with the diluent in a single treatment bag 14 is designing the stopper socket 60 of the highly toxic material vial 54 and the closure barb 24 of the single treatment diluent bag 14 so that the two are incompatible whereby should a vial 54 be inadvertently interconnected with the port 18 of a single treatment diluent bag 14 the closure barb 24 and the stopper socket 60 would not be interengaged and removal of the closure 22 from the inner end of the port 18 would not result in simultaneous removal of the stopper 58 from the vial 54 of highly toxic material and there would be no intermixing of the highly toxic material with the diluent 16 and no administration of a highly toxic mixture to a patient.

While there have been shown and described several forms of safety packaging improvements for vials of highly toxic material, it will be obvious to those skilled in the art that further modifications and improvements may be made without departing from the invention, and it is intended by the appended claims to cover all such modification and improvements as fall within the true spirit and scope of this invention.

We claim:

1. A packaging arrangement for mixing a medicament with a diluent in a multiple treatment bag having an inlet port with a closure member, comprising:

a vial having a neck portion with a shoulder and defining an opening for containing said medicament;

stopper means for sealing said opening of said vial, said stopper means defining means for connecting said closure member of said multiple treatment bag with said stopper means for removing said stopper means from said opening;

plastic cover means for encasing said vial and said stopper, said cover means including an imperforate bottom shroud portion, a lower cover portion and an upper cover portion so that said vial is completely encased by said cover means, said upper cover portion being frangibly removable for uncovering said stopper to permit said vial to be connected with the inlet port of said multiple treatment bag so that said medicament can be mixed with said diluent, said upper cover portion including a non-pierceable wall adjacent said stopper of said vial to preclude insertion of an associated needle into said stopper without removal of said upper cover portion; and an annular sealing member positioned at the shoulder of said neck portion between said vial and said lower cover portion at a region of separation of said removable upper cover portion, said annular sealing member effecting sealing between said vial and said inlet port of said multiple treatment bag after removal of said upper cover portion and connection of said vial to said inlet port.

2. The packaging arrangement in accordance with claim 1, wherein said vial is provided with cooperating thread means fore threadably connecting said vial to said inlet port, said thread means of said vial being connectably incompatible with an associated single treatment bag of diluent.

3. The packaging arrangement in accordance with claim 2, wherein said thread means of said vial are left-handed thread means and are connectably incompatible with the associated single treatment bag.

4. The packaging arrangement of claim 2, wherein said thread means of said vial have a predetermined thread helix and are connectably incompatible with the associated single treatment bag.

5. The packaging arrangement of with claim 1, wherein said connecting means of said stopper means of said vial comprises a socket for connecting said stopper means to said closure member, said socket being connectably non-complementary to an associated single treatment bag of diluent.

* * * * *